United States Patent
Okamura

(10) Patent No.: US 10,634,681 B2
(45) Date of Patent: Apr. 28, 2020

(54) METHOD FOR MEASURING CARDIAC TROPONIN

(75) Inventor: Yoshikazu Okamura, Tokyo (JP)

(73) Assignee: LSI MEDIENCE CORPORATION, Tokyo (JP)

(*) Notice: Subject to any disclaimer, the term of this patent is extended or adjusted under 35 U.S.C. 154(b) by 881 days.

(21) Appl. No.: 14/001,159

(22) PCT Filed: Feb. 24, 2012

(86) PCT No.: PCT/JP2012/054541
§ 371 (c)(1),
(2), (4) Date: Aug. 22, 2013

(87) PCT Pub. No.: WO2012/115221
PCT Pub. Date: Aug. 30, 2012

(65) Prior Publication Data
US 2013/0330841 A1    Dec. 12, 2013

(30) Foreign Application Priority Data

Feb. 25, 2011   (JP) .................................. 2011-039625

(51) Int. Cl.
*G01N 33/68*   (2006.01)

(52) U.S. Cl.
CPC ......... *G01N 33/68* (2013.01); *G01N 33/6887* (2013.01); *G01N 2333/4712* (2013.01)

(58) Field of Classification Search
None
See application file for complete search history.

(56) References Cited

U.S. PATENT DOCUMENTS 5,583,200 A * 12/1996 Larue ................ C07K 14/4716
                                                      435/7.1
5,795,725 A    8/1998 Buechler et al.
(Continued)

FOREIGN PATENT DOCUMENTS

CN         101566634 A    10/2009
JP         9-21804 A       1/1997
(Continued)

OTHER PUBLICATIONS

Collinson, P.O. et al., "Rapid troponin T measurement in whole blood for detection of myocardial damage," Ann. Clin. Biochem., 32:454-458, 1995.
(Continued)

*Primary Examiner* — Gailene Gabel
(74) *Attorney, Agent, or Firm* — Kilpatrick Townsend & Stockton LLLP

(57) ABSTRACT

Disclosed are a method for immunologically measuring cardiac troponin in a biological sample, in which the formation of an immunological complex of cardiac troponin with an antibody specifically binding thereto is performed in the presence of a divalent cation at 4 mmol/L or more; and a kit for measuring cardiac troponin, comprising an antibody specifically binding to cardiac troponin, and a buffer containing a divalent cation at a high concentration. According to the method or the kit, a stable and highly-accurate measured value can be obtained without being affected by interfering substances in a specimen regardless of the type of specimen.

4 Claims, 5 Drawing Sheets

(56) References Cited

U.S. PATENT DOCUMENTS

| | | |
|---|---|---|
| 5,947,124 A | 9/1999 | Buechler |
| 6,156,521 A | 12/2000 | Buechler et al. |
| 6,174,686 B1 | 1/2001 | Buechler et al. |
| 6,248,869 B1 | 6/2001 | Morjana et al. |
| 6,268,481 B1 | 7/2001 | Morjana |
| 6,579,687 B1 | 6/2003 | Buechler et al. |
| 6,627,404 B1 | 9/2003 | Buechler et al. |
| 6,939,678 B1 | 9/2005 | Buechler et al. |
| 6,991,907 B1 | 1/2006 | Buechler et al. |
| 7,723,059 B2 | 5/2010 | Buechler et al. |
| 2001/0006683 A1* | 7/2001 | Riochet .............. C07K 14/4716 424/548 |
| 2003/0211544 A1 | 11/2003 | Buechler et al. |
| 2004/0033529 A1 | 2/2004 | Riochet |
| 2005/0164317 A1* | 7/2005 | Buechler ............ G01N 33/6887 435/7.92 |
| 2010/0167307 A1 | 7/2010 | Buechler et al. |
| 2011/0014629 A1 | 1/2011 | Buechler et al. |
| 2011/0143455 A1 | 6/2011 | Buechler et al. |
| 2012/0129198 A1 | 5/2012 | Buechler et al. |

FOREIGN PATENT DOCUMENTS

| | | | |
|---|---|---|---|
| JP | 2002-502979 A | 1/2002 | |
| WO | 98/29726 A2 | 7/1998 | |
| WO | WO 9829726 A2 * | 7/1998 | ......... G01N 33/6887 |

OTHER PUBLICATIONS

Morjana, N. et al., "Biochemical and immunological properties of human cardiac troponin I fragments," Biotechnol. Appl. Biochem., 33:107-115, 2001.

Extended European Search Report, dated Apr. 7, 2015, EP Application No. 12749915.0, 5 pages.

European Patent Office; Appl. No. EP 12 749 915; Third Party Observations mailed Jan. 22, 2018.

Architect System; Architect Stat Troponin-I; Mar. 2010; pp. 1-8.

501(k) Substantial Equivalence Determination; Decision Summary; Assay Only Template; Pre-market notification; pp. 1-8.

* cited by examiner

METHOD FOR MEASURING CARDIAC TROPONIN

CROSS-REFERENCE TO RELATED APPLICATIONS

This application is a national phase application under 35 U.S.C. 371 claiming priority to PCT/JP2012/054541, filed Feb. 24, 2012, which application claims priority to JP 2011-039625, filed Feb. 25, 2011, the teachings of which are hereby incorporated by reference in their entireties for all purposes.

TECHNICAL FIELD

The present invention relates to a method and a kit for measuring cardiac troponin in a specimen with high accuracy.

BACKGROUND ART

It is known that troponin is a myofibrillar protein complex composed of troponin I, troponin T, and troponin C, and interacts with actin and myosin to contribute in the regulation of muscle contraction by calcium ions. More particularly, when the impulse reaches the level of the motor endplate of the muscle, action potential is generated and transmitted to the sarcoplasmic reticulum. Then, calcium ions are released into the cytosol, and bind to troponin C. A conformational change of the troponins I, T, and C complex occurs by enhancing the interaction between troponin I and troponin C, and it enables muscle contraction by the actin-myosin interaction.

When cardiac muscle is irreversibly damaged, the cardiac troponin that is released appears in the blood stream. Three subunits, i.e., cardiac troponin I, cardiac troponin C, and cardiac troponin T, alone or as a complex (cardiac troponin) consisting of two or three different subunits, exist in the blood.

A blood sample (serum, plasma, or whole blood) is commonly used to evaluate various cardiac troponins. However, such a selection may be limited by the method used. For example, it is known that a serum is an inappropriate biological sample in a method for rapidly evaluating cardiac troponin, and that whole blood complicates the implementation of a quantitative assay. In an immunological assay using heparinized plasma or heparinized whole blood, even when the performance of the method used is very high, unreliable results are often obtained. In general, this problem occurs when the concentration of cardiac troponin in plasma is not very high (non-patent literature 1). Actually, it is known that the presence of heparin in a blood sample interferes with various immunological assays and affects the measurement results. Because of this, the clinical diagnosis of a doctor may be modified.

An EDTA blood collection tube is also commonly used as an anticoagulant, EDTA plasma or EDTA whole blood may cause unreliable results. In general, cardiac troponin I forms a complex with cardiac troponin C and/or cardiac troponin T in the presence of calcium ions. However, in the presence of EDTA, since calcium ions are chelated, the complex containing cardiac troponin I decomposes. As a result, it is known that EDTA plasma or EDTA whole blood affects an immunological assay due to a change in the form of cardiac troponin I in blood (non-patent literature 2).

With respect to a method for avoiding the influence of interfering substances in a specimen in a cardiac troponin assay, an immunological measuring method characterized in that it is carried out using a biological sample containing heparin in the presence of hexadimethrine bromide (polybrene) is disclosed (patent literature 1). This relates to a method for avoiding the interference caused by heparin, and this literature does not refer to EDTA.

Further, it is disclosed that the addition of a divalent cation to cardiac troponin is effective in stabilizing the cardiac troponin complex (patent literatures 2, 3, and 4).

For example, patent literature 2 discloses a composition containing calcium chloride or magnesium chloride at a concentration of 100 μmol/L to 100 mmol/L, as a buffer for a stable composition of troponin complex, and an embodiment containing 2 mmol/L calcium chloride, as a preferable composition (paragraph [0013]). However, patent literature 2 does not refer to the concentration of calcium chloride or magnesium chloride in a reaction solution during the troponin assay (i.e., when the immunological complex is formed). Therefore, it is not disclosed nor suggested in patent literature 2 that a high concentration should be maintained in the reaction solution for the immunological measurement of cardiac troponin, and that an accurate value sometimes cannot be obtained at a low concentration (for example, 2 mmol/L) depending on the type of specimen.

Patent literature 3 discloses that, as a preferable composition of stabilized troponin I, the concentration of calcium chloride or magnesium chloride is 0.01 mmol/L to 10 mmol/L. Further, it is disclosed in Example 14 that calcium chloride is added to a serum or plasma so as to become a final concentration of 6 mmol/L before carrying out an antigen-antibody reaction, the resulting solution is incubated at room temperature for 2 hours followed by 4° C. overnight, and the incubated sample is diluted with a metal-free assay buffer via a dilution factor of 2 to 256 (maximum). In this procedure, calcium chloride is present in the reaction solution at approximately 3 mmol/L or less. However, it is not disclosed nor suggested that a high concentration should be maintained in the reaction solution for the immunological measurement of cardiac troponin, and that an accurate value sometimes cannot be obtained at a low concentration (for example, approximately 3 mmol/L) depending on the type of specimen. In connection with this, the calcium chloride concentration in the troponin assay buffer used in the Examples of patent-literature 3 is 2 mmol/L (for example, Examples 10 to 12).

Patent literature 4 discloses that the concentrations of calcium ions and magnesium ions are not important as buffers used in the preparation of a troponin complex, but it should be preferably about 20 μmol/L to about 20 mmol/L, and the typical amount of calcium and/or magnesium is about 2 to 5 mmol/L. Although it is not clearly described, it is disclosed in Examples 1 and 2 that about 225 mg/L calcium chloride or other calcium salts capable of providing 1 to 3 mmol/L calcium ions are contained in the reaction solution for the preparation of a complex. However, patent literature 4 does not refer to the concentration of calcium chloride or magnesium chloride in a reaction solution during the troponin assay. Further, it is not disclosed nor suggested that a high concentration should be maintained in the reaction solution for the immunological measurement of cardiac troponin, and that an accurate value sometimes cannot be obtained at a low concentration (for example, approximately 3 mmol/L) depending on the type of specimen.

As described above, patent literatures 2, 3, and 4 disclose that calcium chloride or magnesium chloride is generally added at a concentration of about 1 to 6 mmol/L for the stabilization of a sample containing troponin complexes, and it is not intended to improve the reliability of the measured value of an immunological reaction.

CITATION LIST

Patent Literature

[Patent literature 1] Japanese Translation Publication (Kohyo) No. 2002-502979
[Patent literature 2] Japanese Unexamined Patent Publication (Kokai) No. 9-21804
[Patent literature 3] Japanese Translation Publication (Kohyo) No. 11-505605
[Patent literature 4] Japanese Translation Publication (Kohyo) No. 2002-508839

Non-Patent Literature

[Non-patent literature 1] P. O. Collison et al., Ann. Cli. Biochem., (1995), 32, pp. 454-458
[Non-patent literature 2] Morijana. N et al., Biotechnol. Appl. Biochem. (2001), 33, 107-115

SUMMARY OF INVENTION

Technical Problem

As described in the Examples described below in detail, the present inventors attempted to measure cardiac troponin contained in biological samples by an immunological method, and found that the measured values varied according to the difference in the type of specimens for measurement prepared from the biological samples.

An object of the present invention is to provide a method and a kit for measuring cardiac troponin in which a stable and highly-accurate measured value can be obtained without being affected by interfering substances in a specimen, regardless of the type of specimen, such as whole blood, a serum, or plasma collected using different blood coagulation inhibitors, when cardiac troponin contained in a biological sample is detected.

Solution to Problem

The present inventors conducted intensive studies under these circumstances and found that a stable and highly-accurate measured value could be obtained in a method for immunologically measuring cardiac troponin contained in a biological sample, without being affected by interfering substances in a specimen, regardless of the type of specimen, by measuring cardiac troponin under the conditions where a divalent cation was added at a high concentration in a reaction solution, and completed the present invention.

The present invention relates to:
(1) a method for immunologically measuring cardiac troponin in a biological sample, characterized by forming an immunological complex of cardiac troponin with an antibody specifically binding thereto in the presence of a divalent cation at 4 mmol/L or more,
(2) a method for reducing divergence between a measured value obtained using a blood sample to which EDTA is added as an anticoagulant, and a measured value obtained using a blood sample other than the EDTA-added blood sample, in an immunological measurement of cardiac troponin in a biological sample, characterized in that an immunological complex of cardiac troponin with an antibody specifically binding thereto is formed in the presence of a divalent cation,
(3) the method of (1) or (2), wherein the divalent cation is a calcium ion or a magnesium ion,
(4) the method of any one of (1) to (3), wherein the divalent cation is contained in a sample dilution solution and/or an antibody solution,
(5) the method of any one of (1) to (4), wherein a first antibody and a second antibody which specifically bind to cardiac troponin are brought into contact with the biological sample, and an immunological complex formed by an antigen-antibody reaction is measured,
(6) the method of (5), wherein the first antibody and the second antibody recognize different epitopes, and
(7) a kit for measuring cardiac troponin, for the method of any one of (1) to (6), said kit comprising an antibody specifically binding to cardiac troponin, and a buffer containing a divalent cation at a high concentration.

Advantageous Effects of Invention

According to the method or the kit of the present invention, cardiac troponin in a biological sample can be stably and accurately measured, regardless of the type of specimen, without being affected by interfering substances in the specimen.

DESCRIPTION OF EMBODIMENTS

Figure 1:
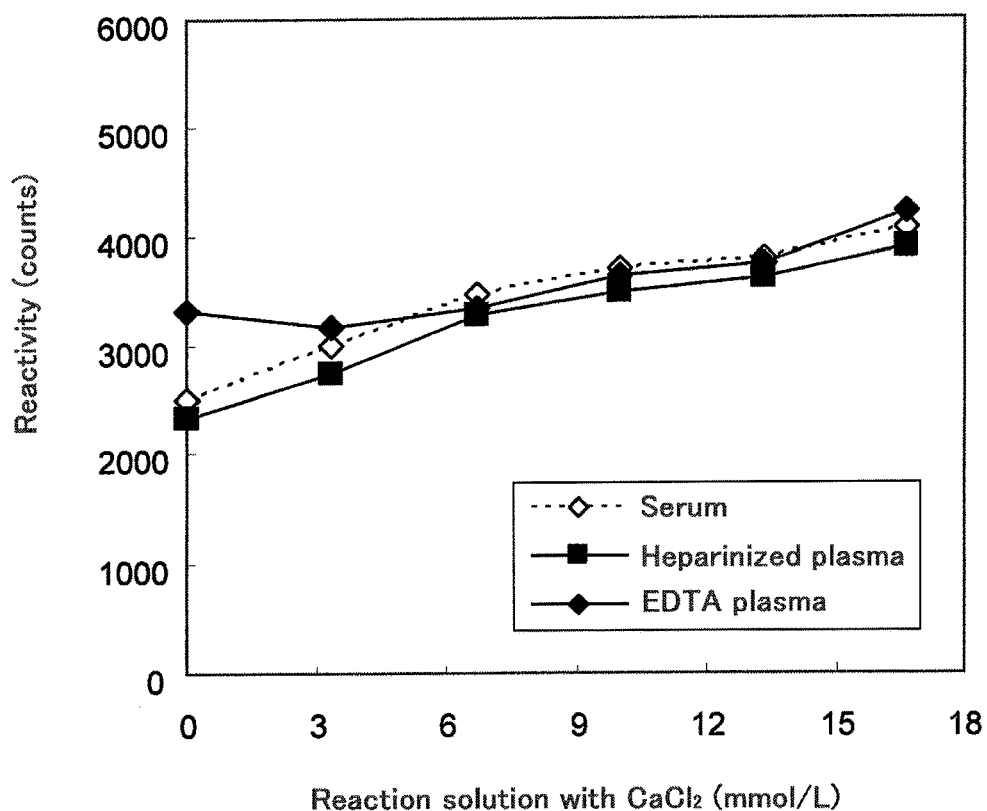
FIG. 1 is a graph showing the result obtained by measuring specimens, using the first antibody recognizing the 41-49 amino acid sequence of cardiac troponin I and the second antibody recognizing the 71-116 amino acid sequence of cardiac troponin I, under the conditions at calcium chloride concentrations of 0 mmol/L, 3.3 mmol/L, 6.7 mmol/L, 10.0 mmol/L, 13.3 mmol/L, and 16.7 mmol/L. The specimens were prepared by adding a cardiac troponin complex (I-T-C) to each of a serum, heparinized plasma, and EDTA plasma collected from a single healthy person.

The biological sample as used herein means a sample which is collected from a human or the like and is suspected of containing cardiac troponin. Examples of the biological sample include blood samples, such as whole blood, a serum, and plasma. A subject from whom a biological sample is collected is not limited, so long as the measurement of cardiac troponin is desired. The subject is preferably a patient suspected of having a myocardial disease, such as myocardial infarction or heart failure.

A specimen which may be used in the present invention is not limited, so long as it is a sample for measurement capable of being prepared from the above-described biological sample. For example, when a blood sample is used, examples of the specimen include a specimen (for example, whole blood, a serum, or plasma) collected using a blood coagulation inhibitor. Examples of the blood coagulation inhibitor include heparin, EDTA, and citric acid. Such an anticoagulant may be used, preferably, by previously adding it to a blood collection tube before blood is collected from a subject such as a human.

Cardiac troponin to be measured in the present invention may be free-form heart troponin I (sometimes abbreviated as cTnI or I), free-form heart troponin T (sometimes abbreviated as cTnT or T), or free-form heart troponin c (sometimes abbreviated as cTnc or c); in a dimer form thereof (IT, IC, or TC); or in a trimer form thereof (ITC). Unless otherwise specified herein, the term "cardiac troponin" refers completely to all these forms, and the term "cardiac troponin complexes" refers entirely to the dimers and the trimer.

An immunological measuring method which may be used in the present invention is not limited, so long as it is a known method using one or more antibodies specific for cardiac troponin. Examples of the method include turbidimetric immunoassay (TIA), enzyme immunoassay (EIA), radioimmunoassay (RIA), a latex agglutination method, fluorescence immunoassay, and immunochromatography. More particularly, it is a method in which an immunological complex of cardiac troponin contained in a specimen with an antibody specific to cardiac troponin is formed in a reaction solution, and a signal derived from the formation is appropriately detected to detect the presence of cardiac troponin. The antibodies may be selected in accordance with a measuring system. When a quantitative measurement with high sensitivity is carried out, a sandwich immunoassay using two or more antibodies may be selected. The sandwich immunoassay may be carried out in one or more stages (two stages, three stages, or the like).

For example, when cardiac troponin contained in a biological sample is measured as a substance to be analyzed, a specimen prepared from the biological sample as previously described is diluted with a sample dilution solution to prepare a specimen for measurement; the resulting specimen is mixed with an insoluble carrier immobilized with an antibody (first antibody) which specifically binds to cardiac troponin, and another antibody (second antibody) which specifically binds to cardiac troponin and is labeled with a labeling substance, to form an immunological complex; unreacted antibodies and cardiac troponin are removed (B/F separation) from the reaction solution by washing; and the amount of the labeling substance bound to the insoluble carrier is measured.

As the insoluble carrier, a carrier which is conventionally used in the art may be used. Examples of material for the insoluble carrier include polymer materials, for example, latex, rubber, polyethylene, polypropylene, polystyrene, a styrene-butadiene copolymer, polyvinyl chloride, polyvinyl acetate, polyacrylamide, polymethacrylate, a styrene-methacrylate copolymer, poly glycidyl methacrylate, an acrolein-ethylene glycol dimethacrylate copolymer, polyvinylidene difluoride (PVDF), and silicone; agarose; gelatin; erythrocyte; and inorganic materials, for example, silica gel, glass, inert alumina, and magnetic material. These may be used individually, or as a combination of two or more.

The shape of the insoluble carrier may be, for example, a microtiter plate, a test tube, beads, particles, or nanoparticles. Examples of the particles include magnetic particles, hydrophobic particles such as polystyrene latex, copolymer latex particles having a hydrophilic group such as an amino group, a carboxyl group, or the like on its surface, red blood cells, and gelatin particles. In these particles, magnetic particles are most preferable in view of the achievement of a quick and convenient B/F separation. More particularly, magnetic particles of microparticles made of, for example, $Fe_3O_4$, $Fe_2O_3$, or various ferrites; metals such as iron, manganese, nickel, cobalt, chromium, and the like; or alloys such as cobalt, nickel, manganese, and the like may be preferably used. Further, insoluble carriers in which these magnetic particles are immobilized on the surface of, or contained within polymer latex made of polystyrene or the like, gelatin, liposome, or the like may be preferably used.

A method of immobilizing the first antibody on these insoluble carriers is known in the art. The immobilization may be carried out by, for example, a physical adsorption method, a covalent binding method, an ion binding method, or a combination thereof.

A labeling substance is not limited, so long as it is a labeling substance which may be used in a conventional immunoassay. Examples of the labeling substance include an enzyme, a fluorescent substance, a radioactive isotope, and insoluble particles. Examples of the enzyme for labeling include alkaline phosphatase, peroxidase, glucose oxidase, tyrosinase, and acid phosphatase. Examples of the fluorescent substance include fluorescein isothiocyanate (FITC), green fluorescent protein (GFP), and luciferin. Examples of the isotope include $^{125}I$, $^{14}C$, and $^{32}P$.

When the labeling substance is an enzyme, the labeling substance may be measured by carrying out a luminescence, fluorescence, or coloring reaction using a substrate for the enzyme. For example, when the enzyme is alkaline phosphatase, a chemiluminescent substrate, such as CDP-star (registered trademark)(disodium 4-chloro-3-(methoxyspiro{1,2-dioxetane-3,2'-(5'-chloro)tricyclo[3.3.1.1$^{3,7}$]decane}-4-yl)phenyl phosphate), CSPD (registered trademark) (disodium 3-(4-methoxy-spiro{1,2-dioxetane-3,2-(5'-chloro)tricyclo[3.3.1.1$^{3,7}$]decane}-4-yl)phenyl phosphate), AMPPD (registered trademark)(3-(4-methoxyspiro{1,2-dioxetane-3,2'-tricyclo[3.3.1.1$^{3,7}$]decan}-4-yl)phenyl phosphate), APS-5, or the like; a fluorescent substrate, such as 4-methylumbelliferylphosphate or the like; or a coloring substrate, such as p-nitrophenyl phosphate, BCIP (5-bromo-4-chloro-3-indolyl phosphate), NBT (4-nitro-blue tetrazolium chloride), INT (iodo-nitrotetrazolium), or the like may be used as its substrate.

The antibody which specifically binds to cardiac troponin, which may be used in the present invention, is not limited, so long as it is a monoclonal or polyclonal antibody which recognizes an amino acid sequence of cardiac troponin as its epitope. Examples of such an antibody include antibodies recognizing the 13-22, 15-25, 18-22, 16-20, 18-28, 21-30, 22-31, 23-29, 24-40, 25-35, 25-40, 26-35, 27-32, 27-39, 27-40, 27-73, 30-100, 31-34, 41-49, 41-56, 56-61, 71-116, 80-110, 83-93, 85-92, 85-95, 87-91, 88-94, 117-126, 122-139, 130-145, 137-148, 143-152, 148-158, 163-209, 163-210, 169-178, 175-190, 186-192, or 190-196 amino acid sequences of cardiac troponin I. Antibodies recognizing the 21-30, 24-40, 41-49, 71-116, 163-209, or 175-190 amino acid sequences of cardiac troponin I are preferable.

These antibodies may be prepared in accordance with known methods, for example, by immunizing an animal with an antigen, such as troponin I or a troponin complex purified from a human heart, recombinant troponin I prepared in vitro, or the like, and further determining its epitope. The epitope means not only a minimum region an antibody recognizes, but also a region identified as a region an antibody can recognize. The antibody may be an antibody fragment which may be prepared by a known method, such as Fab or the like. These antibodies may be appropriately purchased from, for example, Hytest, MedixBiochemica, Meridian Life science, DAKO, Fitzgerald, Biospacific, or the like.

When two types of antibodies are used in the measurement of the present invention, they are not limited, so long as they can form an immunological complex with cardiac troponin contained in a biological sample. It is preferable that the epitopes recognized by the first and second antibodies are different from each other. A monoclonal antibody and a polyclonal antibody may be used in an appropriate combination thereof. Each of the first and second antibodies may be used, not only alone, but also as a combination of two or more.

The addition of a divalent cation in the present invention is not limited, so long as it is carried out so that the divalent cation is present at least when the first immunological complex of cardiac troponin and an antibody specific to cardiac troponin is formed (in the reaction solution) in the immunological measuring method. More particularly, the divalent cation may be added simultaneously when the immunological complex is formed (to the reaction solution), or alternatively, the divalent cation may be added to a specimen before the immunological complex is formed (before the antibody is brought in contact with the specimen containing cardiac troponin).

The divalent cation to be added is prepared as a solution by dissolving it in a known buffer. The divalent cation solution may be prepared alone as well as with a buffering agent, or together with known substances required for a pretreatment of specimens or reactions. Because it is necessary that the divalent cation is present at least when the immunological complex is formed (in the reaction solution), as described above, the divalent cation may be contained in a buffer or the like which may be present when the immunological complex is formed. The "buffer or the like which may be present when the immunological complex is formed" may be appropriately selected in accordance with a measuring method and apparatus used, and may be, for example, a sample dilution solution, antibody solution (such as a solution containing particles immobilized with antibody, a solution containing labeled antibody, or the like), or the like. The divalent cation may be added to multiple buffers.

Examples of the divalent cation in the present invention include a calcium ion and a magnesium ion. Its form is not limited, so long as it can be present as an ion in the reaction solution, and a salt is preferable. Examples of the salt include calcium chloride and magnesium chloride.

The concentration of the divalent cation in the present invention may be selected, as the concentration when the immunological complex is formed, from 4 mmol/L or higher, preferably 5 mmol/L or higher, more preferably 6 mmol/L or higher, more preferably 8 mmol/L or higher, more preferably 10 mmol/L or higher, more preferably 12 mmol/L or higher, or more preferably 15 mmol/L or higher; and 500 mmol/L or lower, preferably 100 mmol/L or lower, more preferably 50 mmol/L or lower, or more preferably 20 mmol/L or lower, as an appropriate combination thereof. In the present invention, the divalent cation is present in the reaction solution within the above concentration range, regardless of the presence of divalent cations contained in a biological sample. In relation to this, when the concentration of the divalent cation in the reaction solution is too high, an accurate measurement of interest cannot be carried out due to the inhibition of an antigen-antibody reaction, and thus, it is necessary to pay attention. To stably and accurately measure cardiac troponin contained in a biological sample regardless of the type of specimen in accordance with the present invention, it is within the range of design issues to determine the concentration of the divalent cation added in accordance with the amount of cardiac troponin contained in the specimen and the type of divalent cation used.

The concentration of the divalent cation in the present invention is higher than that of the divalent cation contained in the reaction solution in conventional immunological measurement for cardiac troponin. As in the conventional methods, when a divalent cation is not contained at the time of the immunological complex formation, or when a divalent cation is contained, but its concentration is low, as we will show concrete experimental data in the Examples described below, divergence occurs between a measured value obtained using a blood sample to which EDTA is added as an anticoagulant (for example, EDTA plasma or EDTA whole blood, particularly, EDTA plasma) and a measured value obtained using a blood sample other than that (for example, a serum, heparinized plasma, citrated plasma, or whole blood). By contrast, when a divalent cation is present at a high concentration at the time of the immunological complex formation, the difference between the measured values is smaller, or the measured values agree substantially with one another. This difference, which the present inventors have found for the first time, in behavior caused by the difference in the type of specimens based on the presence or absence of EDTA addition is a phenomenon commonly observed even when plural monoclonal antibodies recognizing different epitopes are used (see Examples 3 and 4 described below), and is not a phenomenon unique to the specific monoclonal antibody.

As shown in the Examples below, the concentration of the divalent cation in the present invention can be easily determined by preparing an EDTA-added blood sample and another blood sample, measuring the amount of cardiac troponin contained in each blood sample in the presence of many different concentrations of divalent cations, and determining the concentration range of divalent cations in which the measured values of both samples agree with one another. That is to say, the concentration of the divalent cation in the present invention can be selected from the concentration range in which a measured value obtained using a blood sample to which EDTA is added as an anticoagulant accords with a measured value obtained using a blood sample other than the EDTA-added blood sample.

The kit of the present invention may be used for carrying out the method of the present invention, and contains one or more antibodies which specifically bind to cardiac troponin, and a buffer solution containing the divalent cation.

As the antibody which specifically binds to cardiac troponin, above-mentioned known antibodies may be used, and a monoclonal antibody or a polyclonal antibody may be used. Further, an antibody fragment which maintains the specific binding ability to cardiac troponin, for example, Fab, Fab', F(ab')$_2$, or Fv, may be used for the kit.

The antibody may be used for the kit without any modification, or alternatively, in a form suitable for the immunological techniques utilized. For example, when a latex agglutination immunoassay is utilized, the antibody may be immobilized on a latex carrier; when a high-sensitivity measuring method using magnetic particles is utilized, the antibody may be immobilized on the magnetic particles; when a method using a substrate such as immunochromatography or the like is utilized, the antibody may be immobilized on the substrate; and when labeling with a labeling substance (for example, enzymes, fluorescent substances, chemiluminescent substrates, radioactive isotopes, biotin, and avidin) is necessary, the antibody may be labeled.

The buffer solution containing the divalent cation may be prepared as described above, and Examples of the buffer solution include a solution prepared using a salt such as calcium chloride, magnesium chloride, or the like. It is preferable that the buffer solution is prepared as a sample dilution solution.

The kit of the present invention may contain an instruction manual including explanations as to the procedures for performing an immunological measuring method using the kit of the present invention, or notes as to the storage and handling of the kit per se.

EXAMPLES

The present invention now will be further illustrated by, but is by no means limited to, the following Examples.

Example 1: Preparation of Reagent for Measuring Cardiac Troponin and Measurement Method Example 1-1: Preparation of Reagent for Measuring Cardiac Troponin and Preparation of Samples to be Analyzed A reagent for measuring cardiac troponin I (cTnI) was prepared as a reagent for measuring cardiac troponin.

First antibody solution: A solution containing magnetic particles (JSR corporation) immobilized with an antibody (19C7: HyTest Ltd.) recognizing the 41-49 amino acid sequence of cTnI as its epitope was used.

Second antibody solution: A solution containing a labeled antibody obtained by labeling an antibody (DAKO) recognizing the 71-116 amino acid sequence of cTnI as its epitope with alkaline phosphatase (ALP) by a maleimide method was used.

Luminescence substrate solution: CDP-star (Applied Biosystems, Inc.) was used.

Sample dilution solution: A buffer containing 0.1 mol/L Tris.HCl (8.2), 0.1% BSA, 0.15 mol/L NaCl, calcium chloride or magnesium chloride was used.

B/F washing solution: A buffer containing 0.01 mol/L MOPS (7.5), 0.15 mol/L NaCl, and 0.05% Triton X-100 was used.

These solutions were packaged in a cartridge for automatic measurement applicable to an automatic immunoanalyzer described below.

Samples to be analyzed were prepared by adding a cardiac troponin complex (I-T-C) (HyTest Ltd.), at a concentration of approximately 0.7 ng/mL, to a serum, heparinized plasma, and EDTA plasma collected from a healthy person.

Example 1-2: Measurement Method Using Reagent for Measuring Cardiac Troponin

An automatic immunoanalyzer which is similar to that disclosed in Japanese Patent No. 3,115,501 and capable of automatically performing immunoassay using magnetic particles, was used for the measurement of cardiac troponin. This apparatus is capable of efficiently performing B/F separation by magnetic force in a tip arranged as a unit of liquid suction and discharge, and exhibits high efficiency in washing. The measurement steps of the apparatus are as follows.

A chemiluminescent substrate was used, and emission counts detected by a photomultiplier tube (PMT) were regarded as the measurement results.

Measurement Using Automatic Immunoanalyzer

Each cartridge for automatic measurement is filled with each sample, the sample diluent solution, the solution of magnetic particles (coated with the first antibody), the washing solution for B/F separation, the solution of the second antibody, the substrate solution, and the like, and loaded into the automated analyzer. The following steps are carried out in accordance with the normal procedure:
(1) The sample solution previously adjusted to a predetermined dilution ratio with the sample diluent solution, the solution of magnetic particles, and the solution of the second antibody are mixed to generate an immunological complex by an antigen-antibody reaction.
(2) A B/F separation is carried out to remove unreacted substances as follows. The resulting reaction solution is aspirated into the tip arranged as a unit for aspirating a solution, and the magnetic particles are trapped by contact with a magnet on the outer wall of the tip. The solution is discharged from the tip while the magnetic particles are trapped on the inner wall of the tip. After separation, the washing liquid for the B/F separation held in another reaction vessel is aspirated and discharged to wash the magnetic particles in the tip.
(3) The magnet is removed from the outer wall of the tip to lose the effect of magnetic force. The substrate solution is aspirated and discharged to disperse the magnetic particles trapped on the inner wall of the tip and carry out an enzyme reaction.
(4) The amount of luminescence is measured by PMT.

Example 2: Effect on the Reactivity of Cardiac Troponin by Addition of Calcium Chloride or Magnesium Chloride to Reaction Solution The preparation and measurement of the samples were carried out in accordance with Example 1, except that calcium chloride or magnesium chloride were added to the sample dilution solution so that their concentrations became predetermined concentrations (0, 3.3, 6.7, 10.0, 13.3, and 16.7 mmol/L) in each reaction solution.

Figure 2:
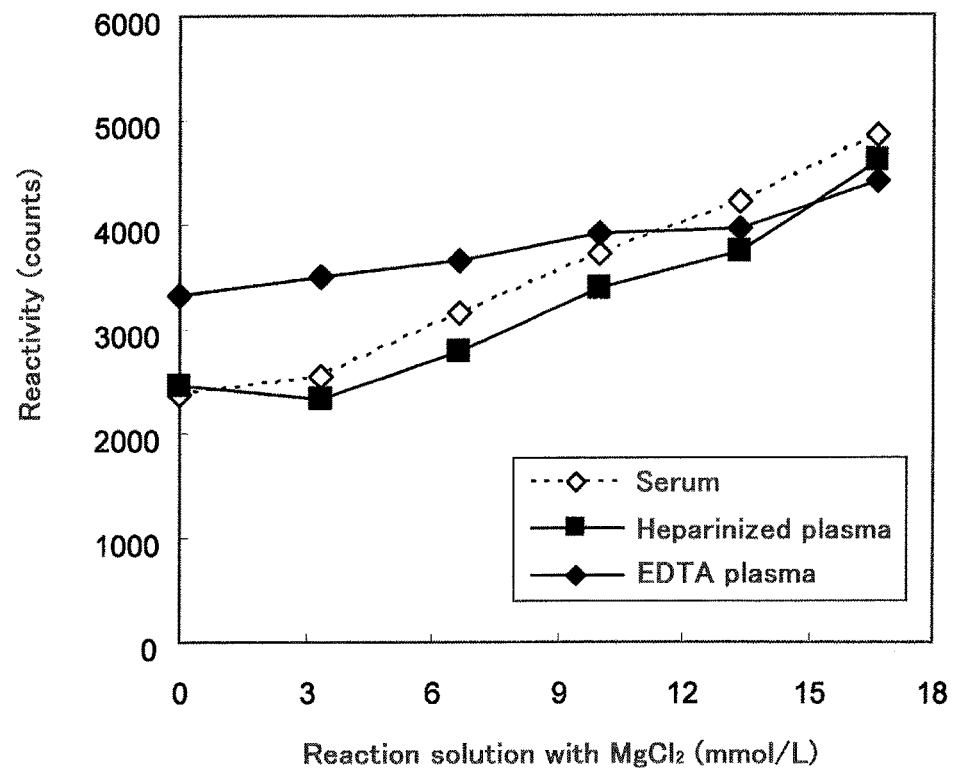
FIG. 2 is a graph showing the result obtained by measuring specimens, using the first antibody recognizing the 41-49 amino acid sequence of cardiac troponin I and the second antibody recognizing the 71-116 amino acid sequence of cardiac troponin I, under the conditions at magnesium chloride concentrations of 0 mmol/L, 3.3 mmol/L, 6.7 mmol/L, 10.0 mmol/L, 13.3 mmol/L, and 16.7 mmol/L. The specimens were prepared by adding a cardiac troponin complex (I-T-C) to each of a serum, heparinized plasma, and EDTA plasma collected from a single healthy person.
Figure 3:
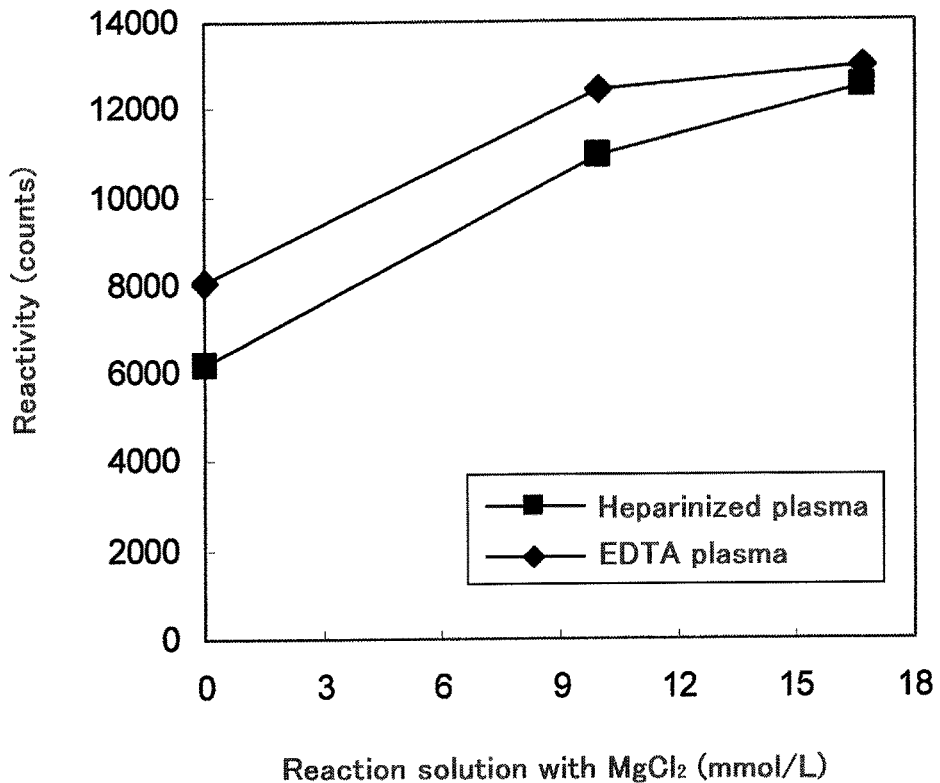
FIG. 3 is a graph showing the result obtained by measuring specimens, using the first antibody recognizing the 41-49 amino acid sequence of cardiac troponin I and the second antibody recognizing the 21-30 amino acid sequence of cardiac troponin I, under the conditions at magnesium chloride concentrations of 0 mmol/L, 10.0 mmol/L, and 16.7 mmol/L. The specimens were prepared by adding a cardiac troponin complex (I-T-C) to each of heparinized plasma and EDTA plasma collected from a single healthy person.
Figure 4:
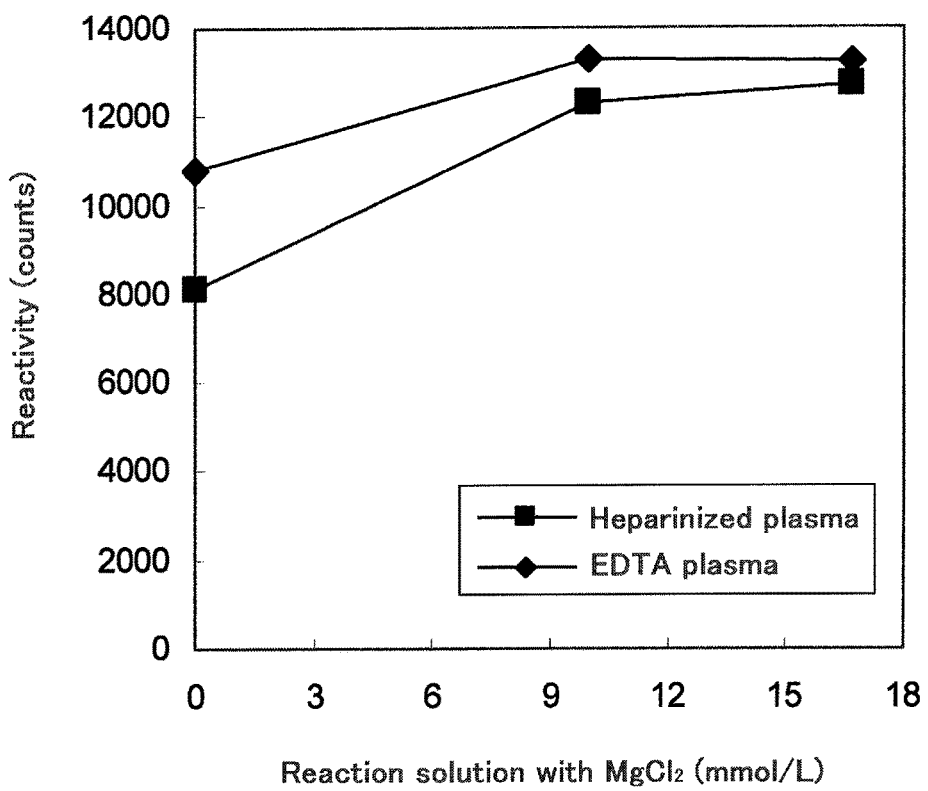
FIG. 4 is a graph showing the result obtained by measuring specimens, using the first antibody recognizing the 41-49 amino acid sequence of cardiac troponin I and the second antibody recognizing the 24-40 amino acid sequence of cardiac troponin I, under the conditions at magnesium chloride concentrations of 0 mmol/L, 10.0 mmol/L, and 16.7 mmol/L. The specimens were prepared by adding a cardiac troponin complex (I-T-C) to each of heparinized plasma and EDTA plasma collected from a single healthy person.

The result when calcium chloride was used is shown in FIG. 1, and the result when magnesium chloride was used is shown in FIG. 2. As a result, it was found that a serum and heparinized plasma were different from EDTA plasma in the reactivity of cardiac troponin, at a conventionally-used low concentration of calcium chloride or magnesium chloride. Further, it was confirmed that the reactivity of cardiac troponin when a serum or heparinized plasma was used accorded with that when EDTA plasma was used, by adding calcium chloride at a concentration of 6.7 mmol/L or more, or magnesium chloride at a concentration of 13.3 mmol/L or more.

As described above, it was found that cardiac troponin can be stably measured in any of the samples by adding calcium chloride or magnesium chloride to the reaction solution at a high concentration. Further, it is considered that a cardiac troponin complex (I-T-C) is disassembled because the calcium ion is chelated in EDTA plasma. Although the cardiac troponin complex (I-T-C) is not disassembled in a serum or heparinized plasma, the reactivity of cardiac troponin for a serum or heparinized plasma accords with the reactivity for EDTA plasma by increasing the divalent cation concentration in the reaction solution, and thus, it is considered that the results obtained in this Example are unexpected results. It is known that calcium ions bind to cardiac troponin C, and cardiac troponin C has multiple binding sites. Therefore, it is considered that the interaction between cardiac troponin I, cardiac troponin T, and cardiac troponin C is changed in the binding state by the concentration of calcium ion. With respect to the effects of the present invention, there is a possibility that the molecular structure of the cardiac troponin complex is changed, by the excessive addition of a divalent cation, to a structure which can impart the same effects as those of free cardiac troponin I.

Example 3: Effect of Different Enzyme-Labeled Antibodies on the Reactivity of Cardiac Troponin by Addition of Magnesium Chloride to Reaction Solution The preparation and the measurement of the samples were carried out in accordance with Example 1, except that the second antibody solution was changed to the following antibodies, and the concentration of magnesium chloride to be added to the reaction solution was changed to the following concentrations. As the second antibody solution, five antibody solutions were prepared using antibodies recognizing, as their epitopes, the 21-30 amino acid sequence (MedixBiochemica), the 24-40 amino acid sequence (Biospacific), the 71-116 amino acid sequence (DAKO), the 163-209 amino acid sequence (DAKO), and the 175-190 amino acid sequence (MedixBiochemica) of cardiac troponin I. The concentrations of magnesium chloride to be added to the reaction solution were 0, 10, and 16.7 mmol/L.

Figure 5:
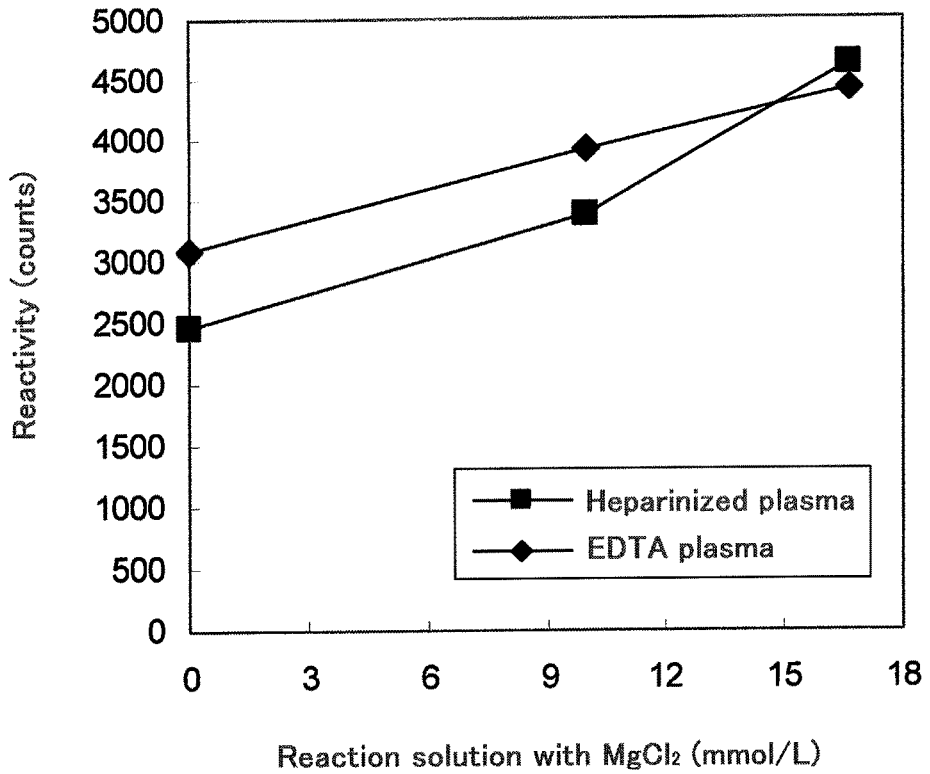
FIG. 5 is a graph showing the result obtained by measuring specimens, using the first antibody recognizing the 41-49 amino acid sequence of cardiac troponin I and the second antibody recognizing the 71-116 amino acid sequence of cardiac troponin I, under the conditions at magnesium chloride concentrations of 0 mmol/L, 10.0 mmol/L, and 16.7 mmol/L. The specimens were prepared by adding a cardiac troponin complex (I-T-C) to each of heparinized plasma and EDTA plasma collected from a single healthy person.
Figure 6:
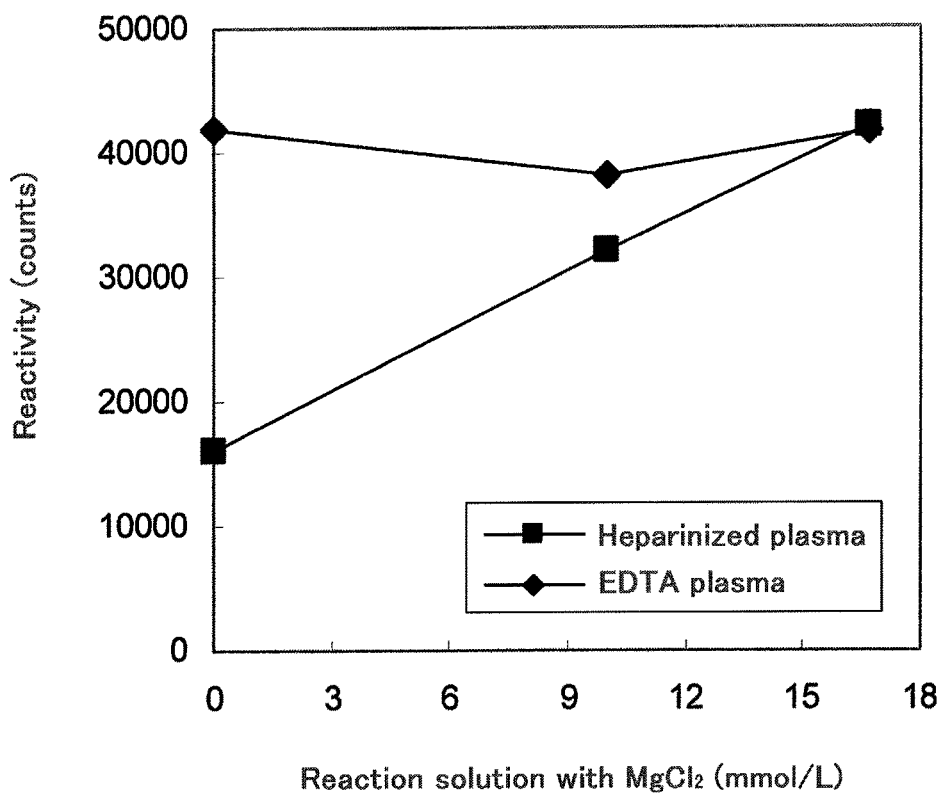
FIG. 6 is a graph showing the result obtained by measuring specimens, using the first antibody recognizing the 41-49 amino acid sequence of cardiac troponin I and the second antibody recognizing the 163-209 amino acid sequence of cardiac troponin I, under the conditions at magnesium chloride concentrations of 0 mmol/L, 10.0 mmol/L, and 16.7 mmol/L. The specimens were prepared by adding a cardiac troponin complex (I-T-C) to each of heparinized plasma and EDTA plasma collected from a single healthy person.
Figure 7:
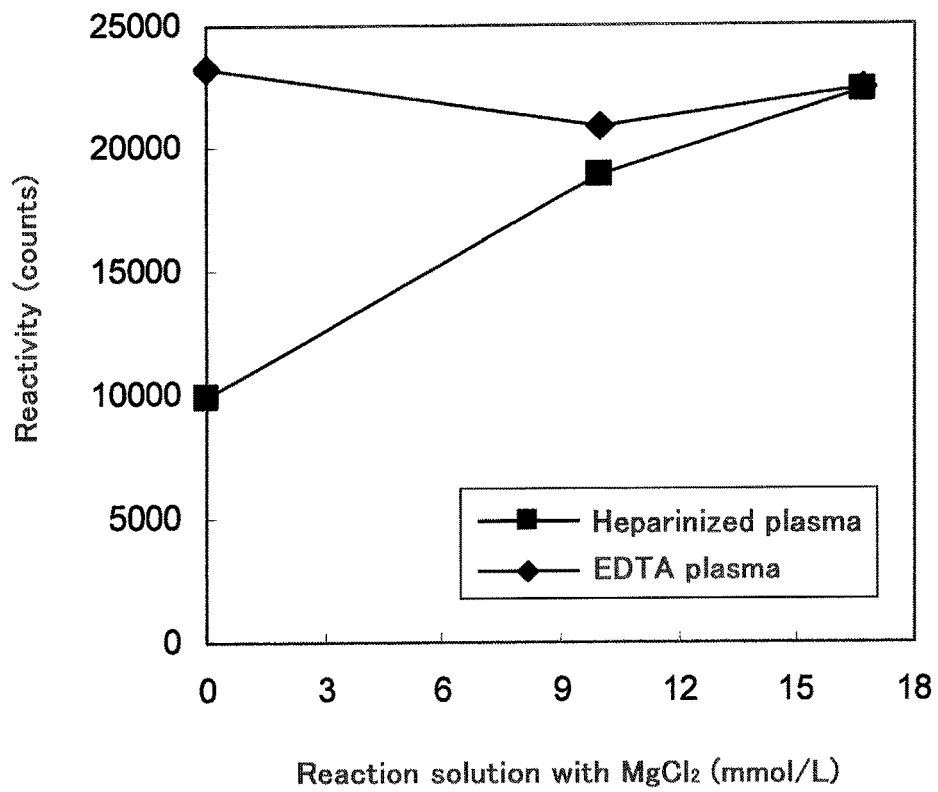
FIG. 7 is a graph showing the result obtained by measuring specimens, using the first antibody recognizing the 41-49 amino acid sequence of cardiac troponin I and the second antibody recognizing the 175-190 amino acid sequence of cardiac troponin I, under the conditions at magnesium chloride concentrations of 0 mmol/L, 10.0 mmol/L, and 16.7 mmol/L. The specimens were prepared by adding a cardiac troponin complex (I-T-C) to each of heparinized plasma and EDTA plasma collected from a single healthy person.

The results when the antibodies recognizing, as their epitopes, the 21-30 amino acid sequence, the 24-40 amino acid sequence, the 71-116 amino acid sequence, the 163-209 amino acid sequence, and the 175-190 amino acid sequence of cardiac troponin I were used as the second antibody solution are shown in FIGS. 3 to 7, respectively. FIGS. 2 and 5 show the results obtained using the same combination of antibodies. As a result, it was confirmed that even when a second antibody solution different in antigen-recognition site from that used in Example 2 was used, the reactivity of cardiac troponin for a serum or heparinized plasma accorded with the reactivity for EDTA plasma by adding magnesium chloride at a concentration of 10 mmol/L or more, as shown in the combination of Example 2.

Example 4: Effect of Different Enzyme-Labeled Antibodies on the Reactivity of Cardiac Troponin by Addition of Calcium Chloride to Reaction Solution The preparation and the measurement of the samples were carried out in accordance with Example 1, except that the second antibody solution was changed to the following antibodies, and the concentration of calcium chloride to be added to the reaction solution was changed to the following concentrations. As the second antibody solution, three antibody solutions were prepared using antibodies recognizing, as its epitope, the 24-40 amino acid sequence, the 71-116 amino acid sequence, and the 163-209 amino acid sequence of cardiac troponin I. The concentrations of calcium chloride to be added to the reaction solution were 0, 6.7, 1and 10 mmol/L.

Figure 8:
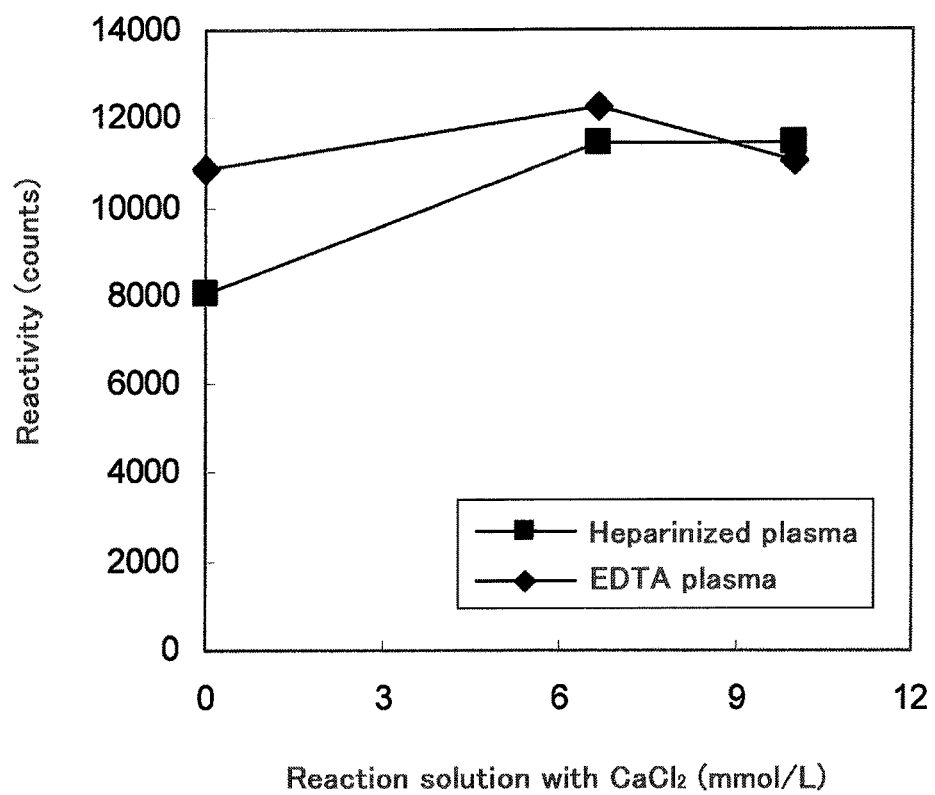
FIG. 8 is a graph showing the result obtained by measuring specimens, using the first antibody recognizing the 41-49 amino acid sequence of cardiac troponin I and the second antibody recognizing the 24-40 amino acid sequence of cardiac troponin I, under the conditions at calcium chloride concentrations of 0 mmol/L, 6.7 mmol/L, and 10 mmol/L. The specimens were prepared by adding a cardiac troponin complex (I-T-C) to each of heparinized plasma and EDTA plasma collected from a single healthy person.
Figure 9:
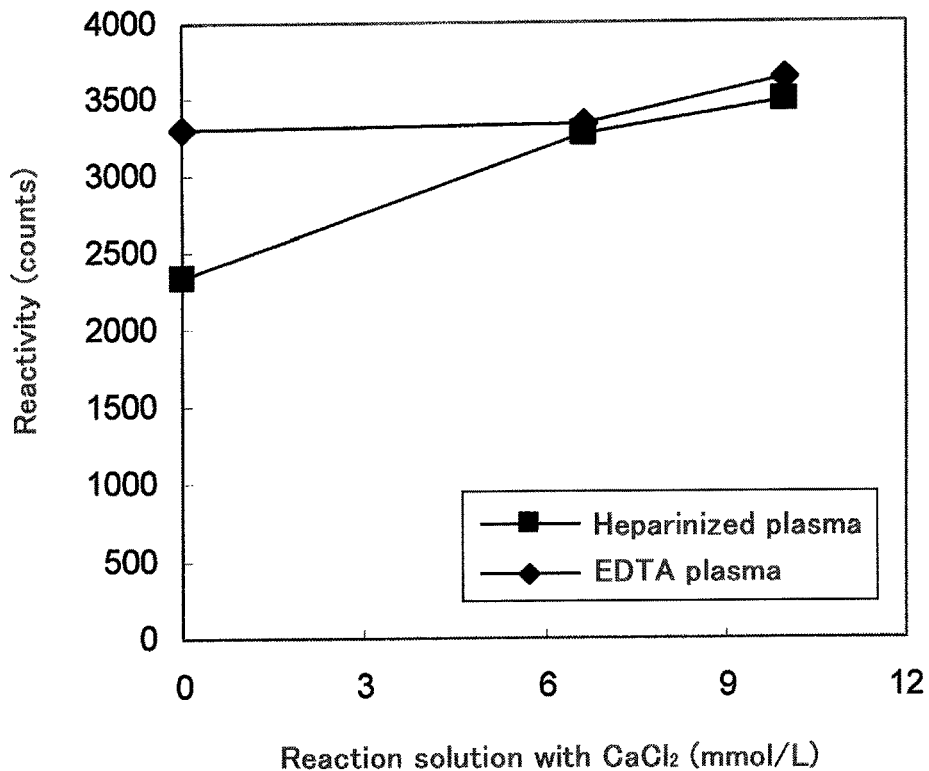
FIG. 9 is a graph showing the result obtained by measuring specimens, using the first antibody recognizing the 41-49 amino acid sequence of cardiac troponin I and the second antibody recognizing the 71-116 amino acid sequence of cardiac troponin I, under the conditions at calcium chloride concentrations of 0 mmol/L, 6.7 mmol/L, and 10 mmol/L. The specimens were prepared by adding a cardiac troponin complex (I-T-C) to each of heparinized plasma and EDTA plasma collected from a single healthy person.
Figure 10:
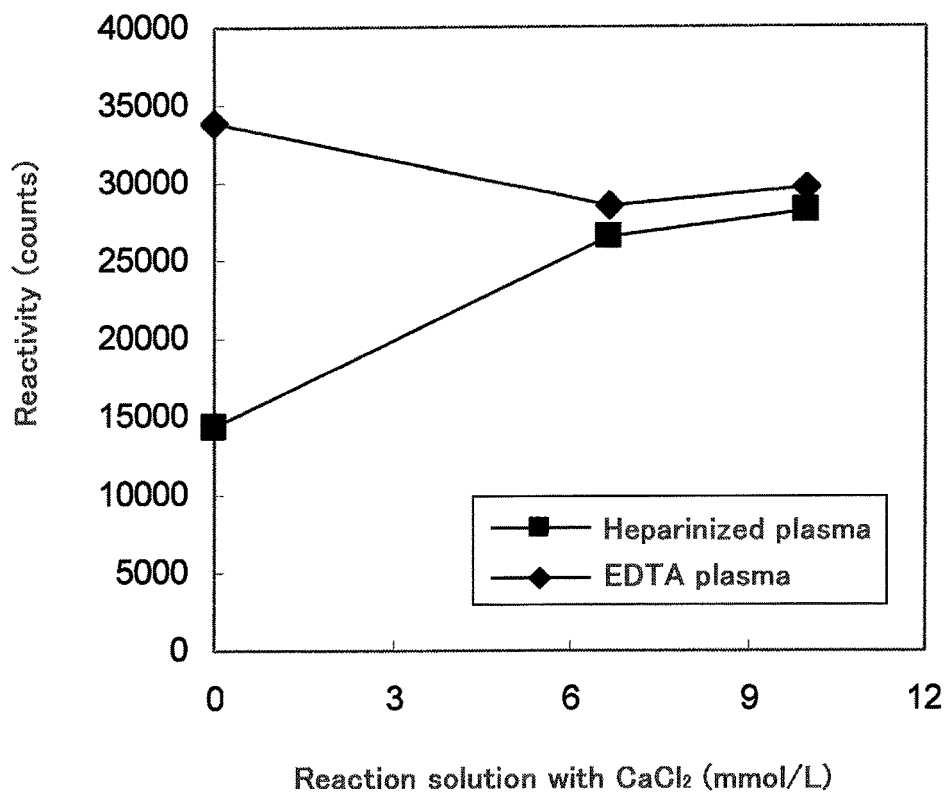
FIG. 10 is a graph showing the result obtained by measuring specimens, using the first antibody recognizing the 41-49 amino acid sequence of cardiac troponin I and the second antibody recognizing the 163-209 amino acid sequence of cardiac troponin I, under the conditions at calcium chloride concentrations of 0 mmol/L, 6.7 mmol/L, and 10 mmol/L. The specimens were prepared by adding a cardiac troponin complex (I-T-C) to each of heparinized plasma and EDTA plasma collected from a single healthy person.

The results when the antibodies recognizing, as its epitope, the 24-40 amino acid sequence, the 71-116 amino acid sequence, and the 163-209 amino acid sequence of cardiac troponin I were used as the second antibody solution are shown in FIGS. 8 to 10, respectively. FIGS. 1 and 9 show the results obtained using the same combination of antibodies. As a result, it was confirmed that even when a second antibody solution different in antigen-recognition site from that used in Example 2 was used, the reactivity of cardiac troponin for a serum or heparinized plasma accorded with the reactivity for EDTA plasma by adding calcium chloride at a concentration of 6.7 mmol/L or more, as shown in the combination of Example 2.

It was suggested from the results of Examples 3 and 4 that the effects of the addition of a divalent cation to the reaction solution were not caused by the change in a structure specified by any one of the 21-30 amino acid sequence, the 24-40 amino acid sequence, the 71-116 amino acid sequence, the 163-209 amino acid sequence, or the 175-190 amino acid sequence of cardiac troponin I. Therefore, it was considered that the reactivity of cardiac troponin for a serum or heparinized plasma accords with the reactivity for EDTA plasma by adding a divalent cation at a high concentration, based on another action different from a previously-proposed action, i.e., the stabilization of the cardiac troponin by the addition of a divalent cation.

INDUSTRIAL APPLICABILITY

According to the present invention, when cardiac troponin is detected, stable and highly-accurate measured results can be obtained without being affected by interfering substances in a specimen regardless of the type of specimen. Since cardiac troponin is used as a marker for myocardial disorders such as myocardial infarction, it should be measured conveniently and quickly, and it is measured in the POCT field or the like as well as a laboratory. For example, when a blood sample is treated, various containers for collecting such samples are used, and therefore, the present invention in which stable and highly-accurate measured results can be obtained regardless of the type of specimen obtained is very useful.

Although the present invention has been described with reference to specific embodiments, various changes and modifications obvious to those skilled in the art are possible without departing from the scope of the appended claims.

The invention claimed is:

1. A method for immunologically measuring cardiac troponin in a biological sample, said method comprising: forming an immunological complex of cardiac troponin with an antibody specifically binding thereto in the presence of a divalent cation during the formation of the immunological complex of cardiac troponin with the antibody, wherein when the divalent cation is a calcium ion, the formation is carried out in the presence of the calcium ion at a concentration higher than 10 mmol/L, or when the divalent cation is a magnesium ion, the formation is carried out in the presence of the magnesium ion at 13.3 mmol/L or more.

2. The method according to claim 1, wherein the divalent cation is contained in a sample dilution solution and/or an antibody solution.

3. The method according to claim 1, wherein a first antibody and a second antibody which specifically bind to cardiac troponin are brought into contact with the biological sample, and an immunological complex formed by an antigen-antibody reaction is measured.

4. The method according to claim 3, wherein the first antibody and the second antibody recognize different epitopes.

* * * * *